US009526639B2

(12) United States Patent
Hansen et al.

(10) Patent No.: US 9,526,639 B2
(45) Date of Patent: Dec. 27, 2016

(54) MEDICAL DEVICE HAVING MAGNETICALLY EXPANDABLE FRAME

(71) Applicant: Cook Medical Technologies LLC, Bloomington, IN (US)

(72) Inventors: Palle M. Hansen, Bjaeverskov (DK); Torben P. Andersen, Taastrup (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 14/709,067

(22) Filed: May 11, 2015

(65) Prior Publication Data
US 2015/0328022 A1 Nov. 19, 2015

(30) Foreign Application Priority Data

May 13, 2014 (GB) .................................. 1408479.2

(51) Int. Cl.
*A61F 2/06* (2013.01)
*A61F 2/844* (2013.01)
*A61F 2/01* (2006.01)
*A61F 2/915* (2013.01)
*A61B 17/12* (2006.01)
*A61F 2/90* (2013.01)

(52) U.S. Cl.
CPC ......... *A61F 2/844* (2013.01); *A61B 17/12022* (2013.01); *A61F 2/01* (2013.01); *A61F 2/90* (2013.01); *A61F 2/915* (2013.01); *A61F 2002/016* (2013.01); *A61F 2002/018* (2013.01); *A61F 2210/009* (2013.01)

(58) Field of Classification Search
CPC ....... A61F 2/90; A61F 2/915; A61F 2210/009
See application file for complete search history.

(56) References Cited

U.S. PATENT DOCUMENTS

| 5,653,747 | A | * | 8/1997 | Dereume | ................ | A61F 2/90 |
| | | | | | | 623/1.54 |
| 6,673,104 | B2 | * | 1/2004 | Barry | ....................... | A61F 2/91 |
| | | | | | | 600/12 |
| 7,722,668 | B2 | | 5/2010 | Moaddeb et al. | | |
| 8,449,604 | B2 | | 5/2013 | Moaddeb et al. | | |
| 2006/0212113 | A1 | | 9/2006 | Shaolian et al. | | |
| 2009/0287293 | A1 | | 11/2009 | Mailhot, Jr. | | |
| 2011/0257724 | A1 | | 10/2011 | Kantor | | |

OTHER PUBLICATIONS

Extended European Search Report dated Sep. 18, 2015.
Combined Search and Examination Report from Great Britain dated Nov. 6, 2014.

* cited by examiner

*Primary Examiner* — Brian Dukert
(74) *Attorney, Agent, or Firm* — Brinks Gilson & Lione

(57) ABSTRACT

A stent, for example, is provided with a plurality of frame elements, which may have an undulating form. The stent is provided with a plurality of magnetic elements between adjacent stent elements. The magnetic elements on opposing circumferentially facing portions or sides of the strut elements have the same polarities so as to produce repulsive forces biasing the stent structure into a radially expanded configuration. The magnetic elements provide an alternative opening force on the stent, enabling the stent to be made of struts of thinner and weaker material or of a non-sprung material. The magnetic elements also provide a constant opening force in order to retain the stent reliably in position within a vessel. The stent could be made of a biodegradable material.

20 Claims, 5 Drawing Sheets

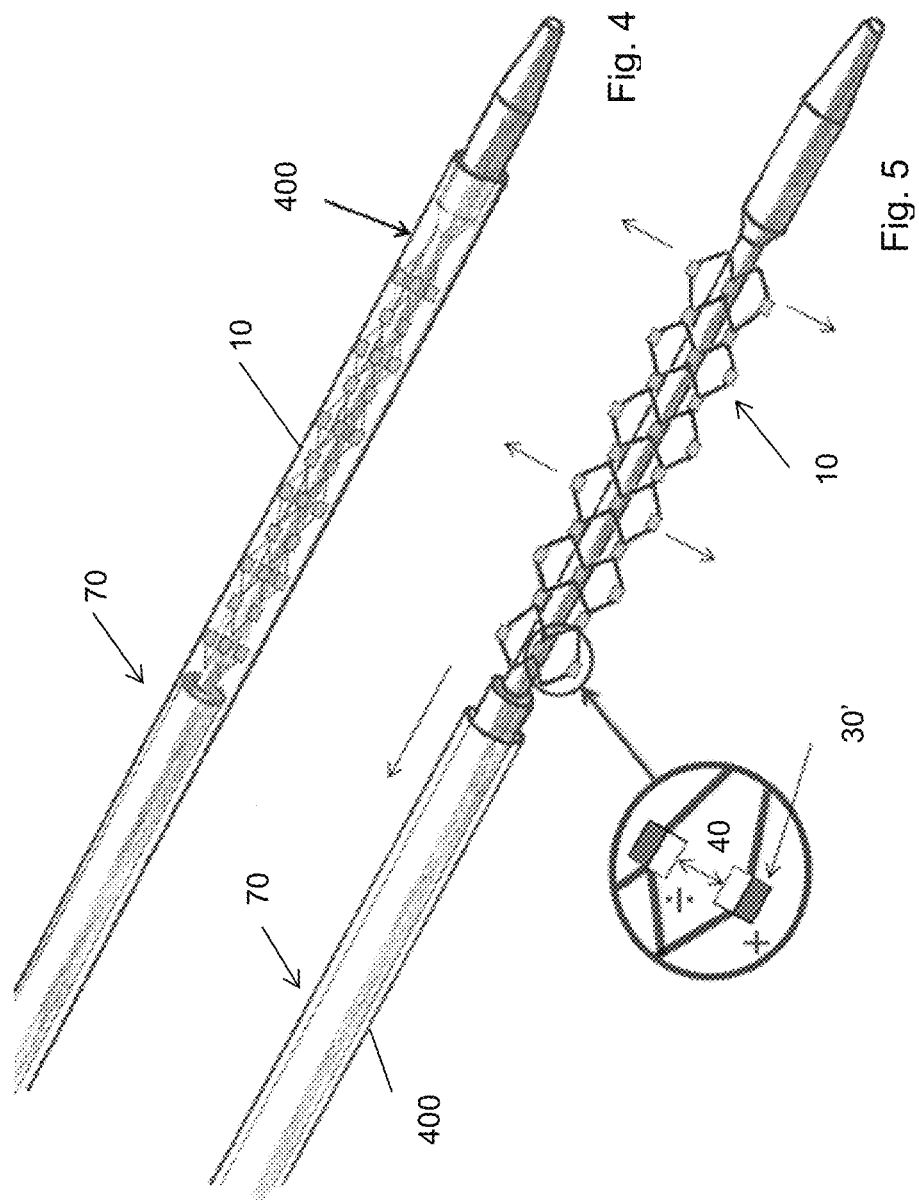

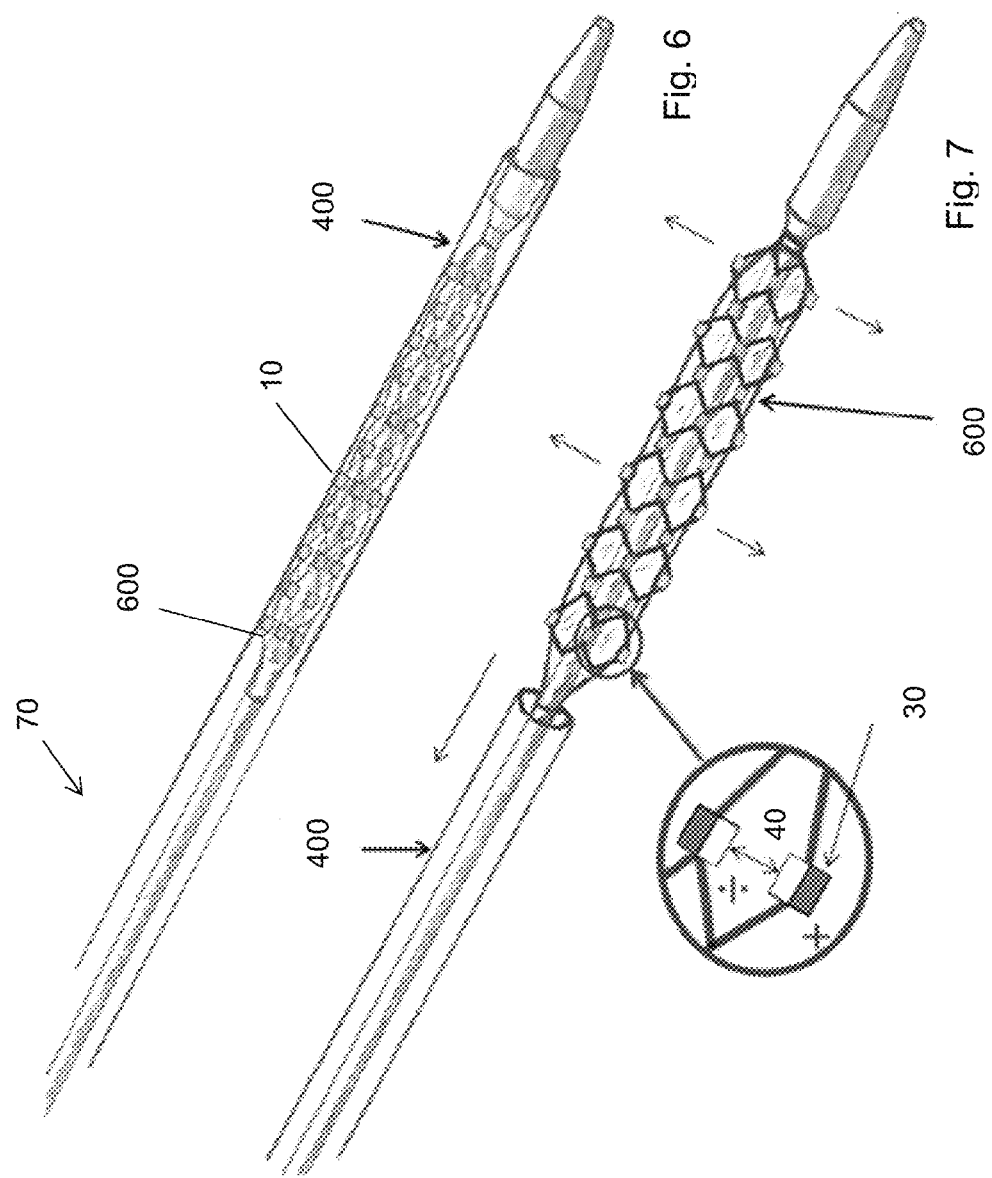

MEDICAL DEVICE HAVING MAGNETICALLY EXPANDABLE FRAME

CROSS-REFERENCE TO RELATED APPLICATIONS

This application claims the benefit of priority under 35 U.S.C. §119(a) to Great Britain Patent Application No. 1408479.2, filed on May 13, 2014, which is incorporated herein by reference in entirety.

TECHNICAL FIELD

The present invention relates to magnetically expandable medical apparatus, preferably an implantable medical device, and in the preferred embodiment to a magnetically expandable stent. The teachings herein are also applicable to a filter, occluder and other implantable medical devices.

BACKGROUND ART

Implantable medical devices are known in many forms and for treating many medical conditions. Examples include stents, grafts, filters, occluders, valve replacement prostheses and so on. Such devices are generally introduced into the patient endoluminally through a remote percutaneous entry point. In order to achieve this, the medical device is loaded onto a carrier at a distal end of an introducer assembly and held in a radially compressed configuration. The introducer assembly is fed into the patient's vasculature from the percutaneous entry point until its distal end is located at the treatment site. Once so positioned, the medical device is released from the carrier and expanded until the device engages the vessel wall to be held thereby. The device can be of a type which expands automatically, achieved by use of spring material, shape memory material and so on. Other types of device are plastically deformable and expanded by a separate mechanism, for instance by expansion of a delivery balloon on which the device is held in crimped form.

It may be important that the medical device applies, in use, a constant force against the walls of the vessel in which it is located. This ensures good patency to the vessel wall, that is, a good seal between the device and the wall tissue, in order to stop leakage around the device. The application of constant force also may ensure that the device does not migrate or rotate out of alignment over time.

The force produced by the above-mentioned medical devices may be a mechanical force, be it by spring force of the components of the device or by relative mechanical stiffness in the case of a plastically deformable device. This may require the devices to have a certain structural strength and as a result a certain volume of material, resulting in increased device profile and reduced compressibility for delivery purposes. Furthermore, the structure of such devices can impart unnatural forces on the vessel wall, the most common being a vessel straightening force acting against the natural curvature of the vessel and/or excessive expansion pressure on the vessel. Such forces can lead to restenosis of the vessel.

There is also a growing desire to have implantable medical devices which are biodegradable. Polymers and similar materials generally have better biodegradability than metals and metal alloys. However, polymers tend to have worse expansion properties, being generally unable to produce equivalent opening forces relative to their metal and metal alloy counterparts, and can also suffer from loss of springiness when kept compressed for any length of time, for instance between loading onto an introducer assembly and eventual deployment into a patient.

Some examples of implantable medical devices are disclosed in US 2011/0257724, US 2006/0212113, U.S. Pat. No. 8,449,604 and U.S. Pat. No. 7,722,668.

SUMMARY OF THE INVENTION

The present invention seeks to provide an improved implantable medical device. The device may be, but is not limited to, a stent or other frame type structure. The device could be used as a vascular stent, as a part of a stent graft or vascular filter, as a part of an occlusion device, as a support frame for a prosthetic valve and so on.

According to an aspect of the present invention, there is provided a medical device, being adapted to generate a magnetic repulsive force, including a support structure having a circumferential periphery extending in a circumferential direction, the support structure including a plurality of interconnected strut elements extending at least partially in a direction normal to the circumferential direction (e.g. along a longitudinal axis), the strut elements being movable relative to one another in the circumferential direction; and a plurality of magnetic elements, the magnetic elements disposed on the strut elements, whereby a circumferentially facing portion or side of each strut element is provided with a first region of first magnetic polarity and an opposing circumferentially facing portion or side of an adjacent strut element is provided with the same magnetic polarity (e.g. a second region of first magnetic polarity) so as to generate a magnetic repulsive force between one another, said magnetic repulsive force acting to bias the strut elements away from one another in the circumferential direction. In other words, the magnetic elements are disposed on adjacent strut elements to provide circumferentially facing sides of adjacent strut elements with the same magnetic polarity.

The provision of repulsive magnetic elements may act to open the support structure, that is to bias it to a radially, or circumferentially, expanded configuration. Thus, magnetic forces can act, at least in some embodiments, in place of mechanical opening forces or at least together with mechanical forces generated by the support structure. Magnetic forces of this nature may ensure that there is a constant opening force in the support structure, useful in ensuring patency with the vessel wall, that is, effective coupling of the medical device to the vessel wall. They may also enable the medical device to adjust to changes in the vessel shape or size over time or as a result of patient movement or bodily functions. Furthermore, the provision of magnetic opening forces reduces the need to have a support structure which has substantial mechanical strength, that is, compared to prior art structures, with the result that the structure can be made thinner and with less material. A thinner structure can be radially compressed to a greater extent, improving endoluminal deployment, enables a reduction in the volume of foreign material in the patient and can also have enhanced biodegradability. In addition, a thinner structure uses less material and thus reduces the amount of foreign material that is implanted in the patient. Moreover, it is possible to use materials that are softer, such as polymer materials.

Providing circumferentially facing sides of adjacent strut elements with a single magnetic polarity helps to avoid longitudinal slippage between strut elements when the support structure is in its compressed form. In other words, opposing magnetic polarities are physically separated from one another by strut elements, thereby reducing the possibility of undesirable magnetic attraction.

Preferably, the device is an implantable medical device, for example being or including a stent. In other examples, the device could be a stent graft, a filter, an occlusion device, a replacement valve prosthesis or any other type of implantable medical device.

It is not excluded, in other examples, that the device may be a part of an introducer assembly, medical tool or the like.

In a practical embodiment, the magnetic elements may be spheroids, rings, or cuboid. In another embodiment, the magnetic elements constitute a part of the strut elements.

The magnetic elements may be formed from paramagnetic material or from permanent magnets.

In an embodiment, adjacent strut elements are connected to one another at strut ends thereof. The strut elements may be arranged in an alternating pattern of coupling and separation of pairs of adjacent strut elements, with adjacent pairs being offset relative to one another. Advantageously, the strut elements are arranged in a rhombus or diamond-shaped array.

The magnetic elements may be disposed at adjacent strut element connections. In some embodiments the magnetic elements could form the strut connecting members of the support structure.

The magnetic elements may comprise magnetic or paramagnetic material having the same polarity within a rhombus formed by the strut elements.

In some embodiments, the medical device may include a filter or occluding barrier carried on the support structure.

In an embodiment, the body member has a tubular or conical shape.

The magnetic elements may be formed of biodegradable material, preferably of a material which will degrade at a rate slower than a rate of ingrowth of vessel tissue.

According to another aspect of the present invention, there is provided a medical device including a support structure having a circumferential periphery extending in a circumferential direction, the support structure including a plurality of interconnected strut elements extending at least partially in a direction normal to the circumferential direction, the strut elements being movable relative to one another in the circumferential direction; and a plurality of magnetic elements disposed on adjacent strut elements, wherein the magnetic elements have the same polarities so as to generate a magnetic repulsive force between one another, said magnetic repulsive force acting to bias the strut elements away from one another in the circumferential direction.

The magnetic elements may be spheroids.

Advantageously, the magnetic elements have a south polarity. In other embodiments, they could have a north polarity.

BRIEF DESCRIPTION OF THE DRAWINGS

Embodiments of the present invention are described below, by way of example only, with reference to the accompanying drawings, in which:

FIG. 4 is a schematic view of the stent of FIG. 1 mounted on a deployment catheter;

FIG. 5 is a schematic view of the stent of FIG. 1 in the process of being deployed into a patient's vessel;

FIG. 6 is a schematic view of the stent of FIG. 1 mounted on a balloon catheter for deployment; and FIG. 7 is a schematic view of the stent of FIG. 1 in the process of being deployed by balloon expansion.

DETAILED DESCRIPTION OF PREFERRED EMBODIMENTS

The embodiments described below are directed to a stent having a generally tubular and cylindrical form, that is, of a type commonly used to treat a variety of vessel defects and ailments. It is to be understood, though, that such a stent could have other forms, for example, to taper along its length, to have one or more waists, even one or more bulging zones, that is, sections designed to extend to a diameter greater than other parts of the stent structure.

The teachings herein are also applicable to other types of medical device, including, for example, filters, embolization coils, as well as devices which include a support structure such as, for example, stent grafts, filters, occlusion devices and the like.

Although the embodiment of stent described below, as will become apparent, has struts formed into an array of rhombi, it will be apparent that the teachings herein are applicable to any structure having one or more strut elements which extend at least in a direction substantially perpendicular to the circumference of the structure and thus able to be biased apart in the circumferential direction by the repulsive magnetic elements provided in the structure, as taught below. In particular, the teachings herein could also be used with stents having zigzag stent frames, filters having radially expandable filter legs and so on.

Figure 1:
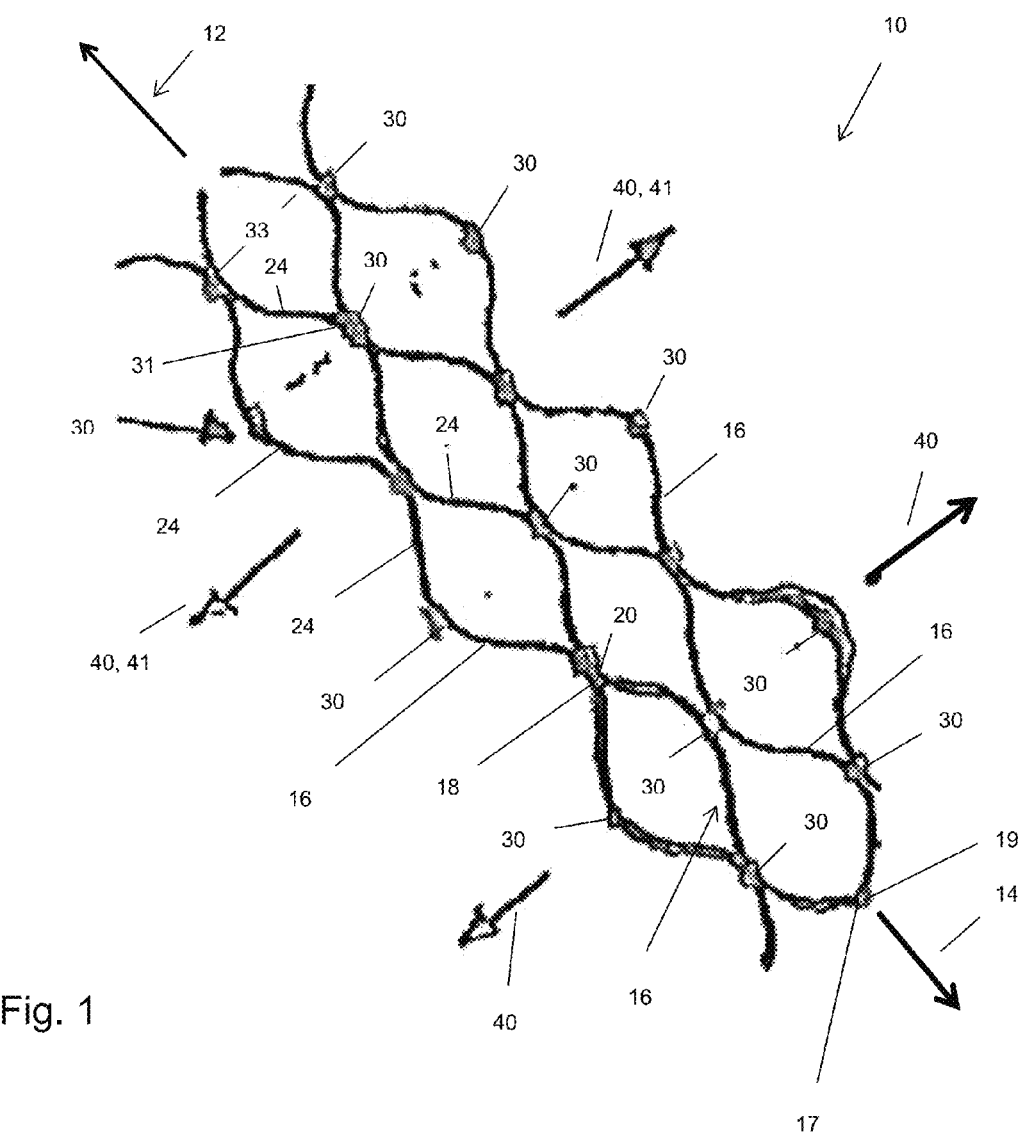
FIG. 1 is a schematic view in perspective of a section of a support structure of an embodiment of stent according to the invention.

Referring now to FIG. 1, this shows a section of the structure of an embodiment of stent 10, which in this example is substantially tubular. The section depicted in FIG. 1 is a part of the surface of the stent and in practice will form a part of the tube of the stent. The axis or longitudinal dimension of the stent is depicted by the arrows 12, 14 in FIG. 1. The circumference 41 of the stent will therefore be in a direction perpendicular to the axis 12, 14.

In this embodiment, the stent 10 is formed of a series of undulating wires 16 (i.e. elongate elements) which extend parallel to the stent axis 12, 14. Adjacent wires are offset relative to one another by 180 degrees such that an apex 18 of one wire 16 is adjacent a trough 20 of the adjacent wire 16. In some embodiments, the strut elements are arranged in an alternating pattern of coupling to (31) and separation of (33) adjacent strut elements, defining a pair of elongate elements (e.g. wires 16) having a plurality of troughs 20 and a plurality of apices 18.

The wires 16 form strut elements 24 between couplings (i.e. connection points 31), described in further detail below. Pairs of elongate elements form a plurality of troughs and apices.

The undulating wires 16 may form a support structure having a circumferential periphery extending in a circumferential direction 41 (e.g. around the support structure). The support structure may include a plurality of interconnected strut elements (struts of wires 16) extending at least partially along the longitudinal axis (12, 14), being normal to the circumferential direction 41. The strut elements being movable relative to one another in the circumferential direction 41.

In addition, a plurality of magnetic elements 30 may be disposed on the strut elements, wherein a circumferentially facing side of each strut element is provided with a first region of first magnetic polarity (FIG. 2, (34A)) and an opposing circumferentially facing side of an adjacent strut element to the circumferentially facing side of each strut element is provided with a second region of first magnetic polarity (FIG. 2, (34B)) so as to generate the magnetic repulsive force between adjacent strut elements, said magnetic repulsive force acting to bias the strut elements away from one another in the circumferential direction (e.g. force 40).

In addition, each elongate member comprises a strut end. For example, the pair of elongate elements may have a first element and a second element, the first element having a first strut end 17, the second element having a second strut end 19. The first strut end 17 may be connected to the second strut end 19. The strut ends may be either at the proximal or distal end of the elongate member. One elongate member of the pair may be connected to an other elongate member of the pair at the respective strut ends thereof. Additionally, all elongate members may be connected at strut ends thereof.

It will be apparent that there will be a series of undulating wires 16 extending around the circumferential periphery of the stent 10.

The wires or other elements forming the structure may be made of metal, metal alloy including a shape memory alloy, or other materials such as polymers. In the preferred embodiment, the structure is biodegradable or bioabsorbable, in particular the structure may be made of a bioabsorbable polymer.

The stent 10 also includes a series of magnetic elements 30 which are attached to or disposed on the frame wires 16 of the stent 10 and in particular are attached to respective ones of adjacent stent struts 24. Magnetic elements 30 may be attached at or form a plurality of connection points 31. In the embodiment shown, the magnetic elements 30 are also attached to the points at which adjacent frame wires 16 come into contact with one another and they may act as the connecting elements themselves. At these connecting points, by virtue of the fact that adjacent frame wires 16 are longitudinally offset relative to adjacent frame wires 16, the magnetic elements are also disposed on adjacent separate strut portions. The magnetic elements 30 have an axis extending from one pole to the other. The axis of the magnetic elements 30 follows the circumference 41 of the stent 10 and is therefore perpendicular or substantially perpendicular to the longitudinal axis 12, 14 of the stent 10.

Figure 2A:
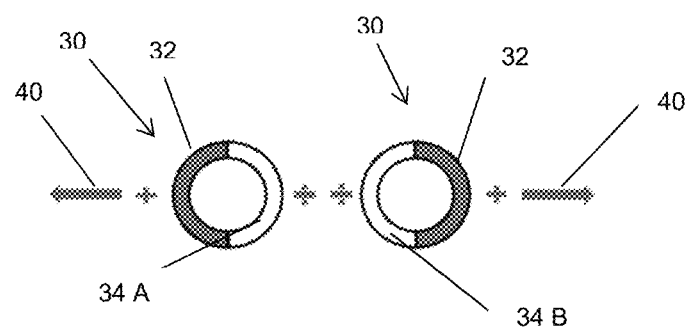
FIGS. 2A to 2C are schematic diagrams of examples of adjacent magnetic elements for the embodiment of FIG. 1.

Referring to FIG. 2A, the magnetic elements 30 are shown as rings in which a first side is positively charged (e.g. forming a first region of first magnetic polarity), for example the side 34A, while the opposite side 32 is negatively charged (e.g. forming a third region of second magnetic polarity). In this embodiment, the first magnetic polarity 34A is provided on the circumferentially facing side of each strut element and the first magnetic polarity 34B is provided on the opposing circumferentially facing side of an adjacent strut element along the longitudinal axis.

Figure 2B:
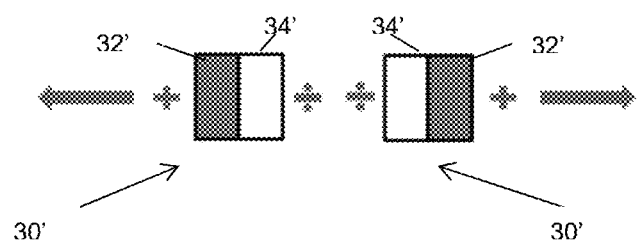

It is not necessary for the magnetic elements 30 to be of such a shape as they could have any suitable shape. FIG. 2B shows magnetic elements 30' which have a generally rectangular cross-section. The magnetic elements 30 could similarly be tubular, rods, and/or have an oblong, circular, square, or rectangular cross-section and so on.

Figure 2C:
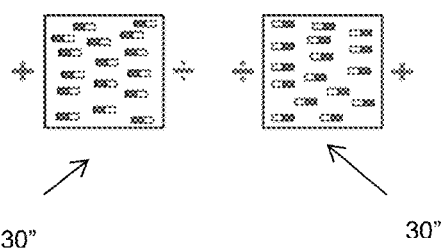

In another embodiment, depicted schematically in FIG. 2C, granular metal particles 30" are embedded into the polymer material of the structure in specific points of need in the frame.

Metal particles 30" could also be included in the entire polymer compound of which the frame is made. The frame can then be magnetized/polarized in the sections where it is needed.

All references to "magnetic elements 30" are hereinafter intended to include reference to the magnetic elements 30' and to the polymer containing the metal particles 30" or to the metal particles 30" themselves as appropriate.

The magnetic elements 30 may be made of any suitable magnetic materials including: NdFeB (neodymium), FeCrCo, SMCo or PtCo.

Where the magnetic material has low biocompatibility, the magnetic elements 30 may be coated with a biocompatible protective coating.

Irrespective of the precise form of the magnetic elements 30 what is important is that adjacent surfaces of adjacent strut elements 24 include magnetic elements 30 having the same polarity (e.g. 34A-B). This may be achieved, for example, by a strut element being provided on one circumferentially facing side with a north polarity (e.g. first region of first magnetic polarity 34A) and the same circumferentially facing side with a south polarity (e.g. third region of second magnetic polarity 32). Adjacent strut elements 24 may also be provided with polarities in a similar manner, but in the opposite orientation (e.g. 34B). This results in circumferentially opposing surfaces of adjacent strut elements 24 being provided with the same polarity (34A-B). As indicated above, this may be achieved in several ways. However, the important aspect is that facing portions of adjacent struts that need to move apart from one another to enable the support structure to expand are provided with magnetism of only the same polarity.

In light of the fact that circumferentially facing magnetic elements 30 each have the same polarity, they will produce a repulsive force between one another, depicted by the arrows 40 in FIGS. 1 and 2. With reference to FIG. 1, repulsive force 40 will push adjacent strut elements 24 away from one another, thereby causing the stent frame formed by the undulating wire elements 16 to expand radially and circumferentially outwardly.

The skilled person will appreciate that as the magnetic elements 30 become more distant from one another, the repulsive force will reduce in strength. Furthermore, in dependence upon the material used for the wire elements 16 and their non-biased shape, it is possible to design a stent 10 having a balance between the opening or expansion force produced by the magnetic elements 30 and the return force produced by the resiliency of the frame elements 16, thereby giving the stent 10 a natural expanded diameter. In other words, when the stent is compressed radially the magnetic elements 30 will produce an expansive force but this force will eventually be counterbalanced by the return force produced by the deformed struts to stop further expansion, thus enabling the design of a stent having a predetermined expanded diameter. This can be advantageous in having a stent which can expand to a vessel wall reliably without imposing upon the vessel wall undue expansion forces.

The structure also permits the design of a stent which will generate a continued expansion force against a vessel wall to hold the stent in place against the vessel and to account for changes in vessel shape and/or size over time and during movement of or within the patient. Such a constant expansion force can be generated by suitable selection of the size of the stent 10 as well as by suitable selection of the frame elements 16, in terms of size, shape and the material used therefor.

The force used by the magnetic elements 30 also enables use of very thin stent struts or strands as well as the use of materials which do not have inherent spring force. In one example, the stent wire 16 could have a thickness in the region of 0.08 mm for a stent having an expanded diameter of between 1.5 to 2 mm. It is the force generated by the magnetic elements 30 which will provide an opening force to such a stent and not any spring forced generated by such struts 24 or strands 16. In another example, the stent wires 16 can be made of a polymer material including bioabsorbable and biodegradable materials such as poly-L-lactic acid (PLLA). Other materials include polyurethane, polyethylene, ultrahigh molecular weight polyethylene such as Dyneema™, polyester, PTFE, silicone and so on.

The use of thinner elements for the stent structure may also reduce the amount of foreign material which is implanted in the body of the patient, and can also lead to faster biodegradation of the structure over time. It is not necessary for the stent or other support structure to be made of a sprung material.

Figure 3:
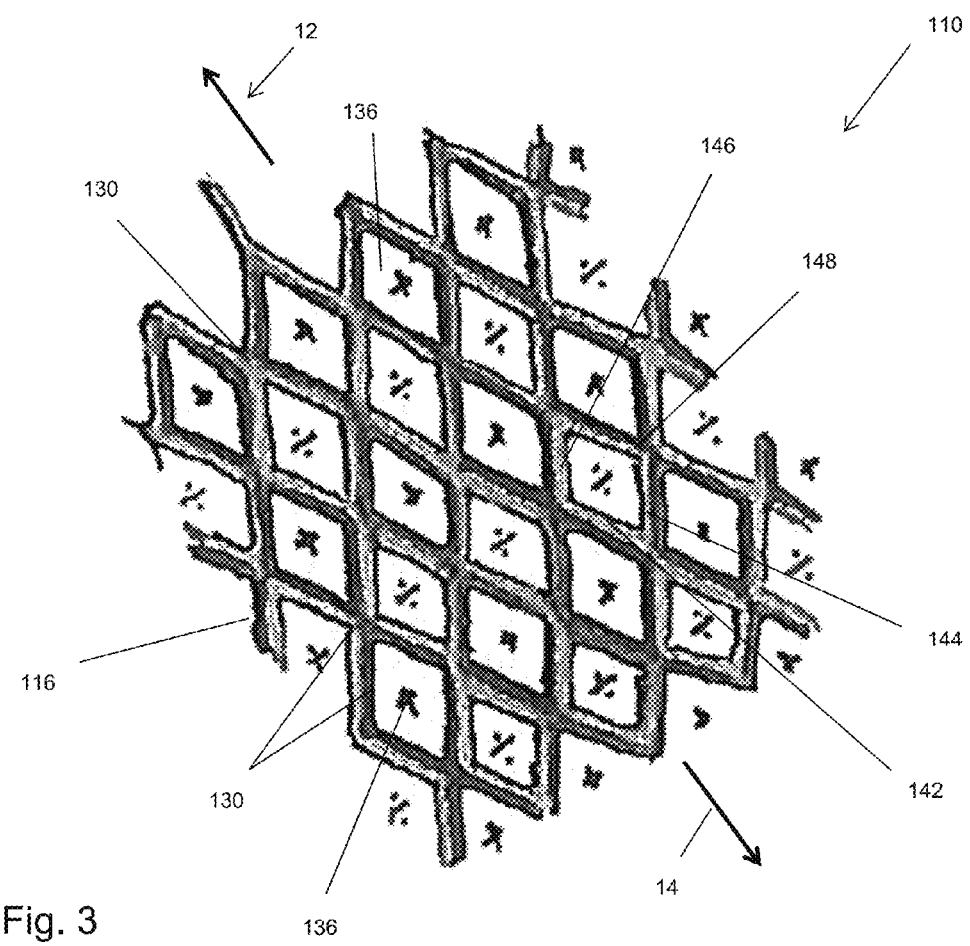
FIG. 3 is a schematic view in perspective of a part of a support structure.

Referring now to FIG. 3, this shows another embodiment of stent 110 and in particular a section of stent similar to the section shown in FIG. 1. In this particular embodiment, the stent 110 has a rhombus or diamond shaped frame structure 116 which may be provided with a polymer coating 130 made of magnetic or paramagnetic material or in another embodiment formed integrally with such material. As with previous embodiments, this embodiment comprises elongate elements or pairs of elongate elements along the longitudinal axis within the frame structure 116. The paramagnetic material is designed to have the same polarisation directions within the diamond shaped areas 136 of the stent structure, so as to generate repulsive forces on the stent frame 116, causing the diamond shape areas to be biased into the expanded configuration shown in FIG. 3.

It will be appreciated that it is not necessary to coat the entirety of the wire elements 142-148 of the frame structure 116 with magnetic material as these can in some embodiments be only partially magnetised, for example at the apices of the diamonds, to produce an arrangement analogous that of the magnetic elements 30 of the embodiment of FIG. 1.

In other embodiments the coating itself may be bipolar, having the same polarity on its outer surface relative to an inner surface. Such an embodiment of core may be part of a structure of the wire elements 16 of the stent 10.

Referring now to FIG. 4, this shows a stent 10 mounted on an introducer assembly 70 and covered by a sheath 400. The stent 10 is held in a radially contracted configuration on the introducer assembly 70 and in a manner similar to that of conventional sprung stents, for example, stents made of a shape memory material or of a spring material. The person skilled in the art will be familiar with such elements of the introducer assembly 70.

FIG. 5 shows the stent 10 once it has been fed endoluminally into a vessel of a patient on the introducer assembly 70 and located at the site of the vessel to be treated. The constraining elements of the introducer assembly 70 (for example the sheath 400) are released, thereby enabling the stent 10 to expand as a result of the repulsive forces produced by the magnetic elements 30 of the stent 10 (or the coating 130 of the stent 110 of FIG. 3), thereby expanding the stent 10 against the vessel wall. The repulsive magnetic forces will continue to press the stent 10 against the vessel wall once deployed and will therefore assist in holding the stent in position after deployment.

Thus, a medical device of such a structure does not need to rely upon the generation of a mechanical force as with conventional medical devices, but instead makes use of constant magnetic repulsion to keep the support structure of the device in its expanded state against the vessel wall. As a result of the use of such magnetic forces it is not necessary to generate large opening forces to hold the device in place. Moreover, the device can in practice be much more flexible and able to configure to the shape of the vessel or other organ, as well as accommodating changes in the vessel during normal body function and over time.

In embodiments where the magnetic elements are formed of paramagnetic material, this can be magnetised after assembly of the stent components, typically by fitting the stent form onto a cylindrical mandril and then magnetising the magnetic elements, typically by an electromagnet or a permanent magnet. Following magnetisation, the stent can be compressed onto an introducer assembly in a manner analogous to stents made of spring material such as spring steel or a shape memory alloy.

It is also envisaged that the stent 10 could be expanded mechanically, for instance by a deployment balloon 600, into the vessel of a patient, in which case the stent 10 will be mounted on a balloon 600 of a balloon catheter 70 as shown in FIG. 6. Once located at the site of the vessel to be treated, the stent is expanded by conventional balloon expansion as shown in FIG. 7, with the magnetic elements 30 acting simply to maintain a certain opening force to retain the stent 10 in position within the vessel. Such a structure could be particularly useful for use in delicate vessels such as the cerebral vessels.

In the case of a filter, this could have a frame with a narrow end and a wide end, with a plurality of struts extending from the narrow end in an outwardly tapering manner towards the wide end. Magnetic elements could be positioned in any suitable location on the struts to generate repulsive forces biasing these apart from one another.

It will be appreciated also that the support structure, stent for instance, could be a part of an assembly such as a stent graft, occluder, prosthetic valve, filter and so on.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in GB 1408479.2, from which this application claims priority, and in the abstract accompanying this application are incorporated herein by reference.

The invention claimed is:

1. A medical device adapted to generate a magnetic repulsive force, the medical device comprising:
   a support structure having a circumferential periphery extending in a circumferential direction, the support structure including a plurality of interconnected strut elements extending at least partially along a longitudinal axis, the longitudinal axis being normal to the circumferential direction, the strut elements being movable relative to one another in the circumferential direction; and
   a plurality of magnetic elements, each magnetic element having a polar axis extending from a first pole to a second pole, the magnetic elements disposed on the strut elements such that the polar axis of each magnetic element follows the circumferential periphery of the support structure, wherein a circumferentially facing side of each strut element is provided with a first region of first magnetic polarity and an opposing circumferentially facing side of an adjacent strut element to the circumferentially facing side of each strut element is provided with a second region of first magnetic polarity so as to generate the magnetic repulsive force between adjacent strut elements, said magnetic repulsive force acting to bias the strut elements away from one another in the circumferential direction.

2. A medical device according to claim 1, wherein the medical device is implantable.

3. A medical device according to claim 2, wherein the medical device includes a stent.

4. A medical device according to claim 1, wherein the support structure is made from a polymer material.

5. A medical device according to claim 1, wherein the strut elements are interconnected at a plurality of connection points, and wherein the first magnetic polarity is provided on the circumferentially facing side of each strut element and the first magnetic polarity is provided on the opposing circumferentially facing side of an adjacent strut element along the longitudinal axis.

6. A medical device according to claim 1, wherein the magnetic elements are spheroids, rings, rods or rectangular cuboids.

7. A medical device according to claim 1, wherein the strut elements comprise the magnetic elements.

8. A medical device according to claim 1, wherein the magnetic elements are formed from paramagnetic material.

9. A medical device according to claim 1, wherein the magnetic elements are permanent magnets.

10. A medical device according to claim 1, wherein the strut elements are arranged in an alternating pattern of coupling to and separation of adjacent strut elements, defining a pair of elongate elements having a plurality of troughs and a plurality of apices.

11. A medical device according to claim 10, wherein the pair of elongate elements comprises a first element and a second element, the first element having a first strut end, the second element having a second strut end, the first strut end being connected to the second strut end.

12. A medical device according to claim 1, wherein the strut elements are arranged to form an array of *rhombi*.

13. A medical device according to claim 10, wherein the strut elements are interconnected at a plurality of connection points, wherein the magnetic elements are disposed at the connection points.

14. A medical device according to claim 12, wherein the magnetic elements comprise magnetic or paramagnetic material, the magnetic or paramagnetic material having a same magnetic polarity within a given rhombus of the array.

15. A medical device according to claim 1, further comprising a filter or occluding barrier disposed on the support structure.

16. A medical device according to claim 13 wherein the magnetic elements form the connection points.

17. A medical device according to claim 1 wherein the circumferentially facing side of each strut element comprises a third region of second magnetic polarity, the third region of second magnetic polarity being oppositely disposed from the first region of first magnetic polarity.

18. A medical device according to claim 17 wherein the first magnetic polarity is one of a north polarity and a south polarity.

19. A medical device according to claim 18 wherein the second magnetic polarity is the other of the north polarity and the south polarity.

20. A medical device according to claim 14 wherein the magnetic elements comprise a polymer coating.

* * * * *